(12) United States Patent
Metselaar et al.

(10) Patent No.: US 7,955,618 B2
(45) Date of Patent: Jun. 7, 2011

(54) COMPOSITION FOR TREATMENT OF INFLAMMATORY DISORDERS

(75) Inventors: Josbert Maarten Metselaar, Utrecht (NL); Marca Henriette M. Wauben, Utrecht (NL); Gerrit Storm, Utrecht (NL)

(73) Assignee: Enceladus Pharmaceuticals B.V., Amsterdam (NL)

( * ) Notice: Subject to any disclaimer, the term of this patent is extended or adjusted under 35 U.S.C. 154(b) by 182 days.

(21) Appl. No.: 10/455,257

(22) Filed: Jun. 5, 2003

(65) Prior Publication Data
US 2004/0037875 A1    Feb. 26, 2004

Related U.S. Application Data

(63) Continuation of application No. PCT/EP01/14633, filed on Dec. 7, 2001.

(51) Int. Cl.
*A61K 9/127* (2006.01)
(52) U.S. Cl. .......... 424/450; 977/801; 977/907
(58) Field of Classification Search .......... 424/450
See application file for complete search history.

(56) References Cited

U.S. PATENT DOCUMENTS

| | | | |
|---|---|---|---|
| 4,370,349 A | 1/1983 | Evans et al. | |
| 4,522,803 A | 6/1985 | Lenk et al. | |
| 4,818,537 A | 4/1989 | Guo | |
| 4,954,345 A | 9/1990 | Muller | |
| 4,994,443 A | 2/1991 | Folkman et al. | |
| 5,139,803 A | 8/1992 | Haynes et al. | |
| 5,190,936 A | 3/1993 | Laugier | |
| 5,192,528 A * | 3/1993 | Radhakrishnan et al. | 424/45 |
| 5,316,771 A | 5/1994 | Barenholz et al. | |
| 5,356,633 A * | 10/1994 | Woodle et al. | 424/450 |
| 5,569,464 A | 10/1996 | Endo et al. | |
| 5,762,918 A | 6/1998 | Thorpe | |
| 5,786,344 A | 7/1998 | Ratain et al. | |
| 5,853,752 A | 12/1998 | Unger et al. | |
| 6,028,066 A | 2/2000 | Unger | |
| 6,090,800 A | 7/2000 | Unger et al. | |
| 6,120,751 A | 9/2000 | Unger | |
| 6,126,966 A | 10/2000 | Abra et al. | |
| 6,316,260 B1 | 11/2001 | Freisleben et al. | |
| 6,403,056 B1 | 6/2002 | Unger | |
| 6,423,735 B1 | 7/2002 | Camden et al. | |
| 6,444,660 B1 | 9/2002 | Unger et al. | |
| 6,511,676 B1 | 1/2003 | Boulikas | |
| 6,562,371 B1 | 5/2003 | Kawahara et al. | |
| 2002/0058060 A1 | 5/2002 | Kan et al. | |
| 2002/0159951 A1 | 10/2002 | Unger et al. | |
| 2003/0050236 A1 | 3/2003 | Dawson et al. | |
| 2003/0054027 A1 | 3/2003 | Unger | |
| 2005/0152962 A1 | 7/2005 | Metselaar | |
| 2009/0226509 A1 | 9/2009 | Metselaar | |

FOREIGN PATENT DOCUMENTS

| | | |
|---|---|---|
| EP | 0 622 072 A2 | 3/1994 |
| EP | 0 622 072 B1 | 11/1994 |
| EP | 1 072 617 A1 | 7/1999 |
| EP | 1 044 679 A1 * | 10/2000 |
| EP | 1 190 706 * | 3/2002 |
| EP | 1 190 706 A1 | 3/2002 |
| JP | 62-42733 | 2/1987 |
| WO | WO94/07466 * | 4/1994 |
| WO | WO 94/07466 | 4/1994 |
| WO | WO 94/07468 | 4/1994 |
| WO | WO 98 42283 | 10/1998 |
| WO | WO 98 50040 | 11/1998 |
| WO | WO 98 50041 | 11/1998 |
| WO | WO 00/25748 A1 | 5/2000 |
| WO | WO 00/38653 | 7/2000 |
| WO | WO 02/45688 A2 | 12/2001 |
| WO | WO 02/45688 A2 | 6/2002 |
| WO | WO 03/105805 A1 | 12/2003 |
| WO | WO 2004 019916 A1 | 3/2004 |

OTHER PUBLICATIONS

PCT International Search Report, PCT/EP01/14633, dated May 8, 2002, 2 pages.
PCT International Preliminary Examination Report, PCT/EP01/14633, dated Apr. 2, 2003, 2 pages.
Al-Muhammad et al., Studies on the formulation and in vitro release of ophthalmic liposomes containing dexamethasone sodium phosphate, J. Microencapsulation, 1996, pp. 123-130, vol. 13, No. 2.
Farshi et al., In-vivo studies in the treatment of oral ulcers with liposomal dexamethasone sodium phosphate, J. Microencapsulation, 1996, pp. 537-544, vol. 13. No. 5.
Vion-Dury et al., Specific in Vitro Labeling of Cells with a Fluorine-19 Probe Ensapsulated in Antibody-Targeted Liposomes: A F-19 NMR Spectroscopy Study, Magnetic Resonance in Medicine, 1993, pp. 252-255, vol. 29, No. 2.
Matselaar et al., Liposomes for Intravenous Drug Targeting: Design and Applications, Mini Reviews in Medicinal Chemistry, 2002, pp. 319-329, vol. 2.
Shibata et al., Preparation and Characterization of Liposomes Incorporating Hydrophobic Poly (Amino Acid)s with Different Secondary Structure, Chemical & Pharmaceutical Bulletin, May 1994, pp. 1151-1153, vol. 42, No. 5. Gonzalez-Rothi et al., Pulmonary Targeting of Liposomal Triamcinolone Acetonida Phosphate, Pharmaceutical Research, 1996, pp. 1699-1703, vol. 13, No. 11.
PCT International Preliminary Examination Report, PCT/NL03/00596, dated Dec. 4, 2003.
PCT International Search Report, PCT/NL03/00596, dated Dec. 7, 2004.
PCT International Preliminary Examination Report, PCT/NL03/00419, Dated Apr. 14, 2004.
PCT International Search Report, PCT/NL03/00419, dated Sep. 8, 2003.
U.S. Appl. No. 12/387,598, filed May 5, 2009, Metselaar, Composition for Treatment of Inflammatory Disorders.

(Continued)

*Primary Examiner* — Carlos A Azpuru
(74) *Attorney, Agent, or Firm* — TraskBritt, P.C.

(57) ABSTRACT

A pharmaceutical composition for parenteral administration, comprising liposomes composed of non-charged vesicle-forming lipids, including up to 20 mole percent of an amphipathic vesicle-forming lipid derivatized with polyethyleneglycol, and optionally including not more than 10 mole percent of negatively charged vesicle-forming lipids, the liposomes having a selected mean particle diameter in the size range between about 40-200 nm and containing a water soluble corticosteroid for the site-specific treatment of inflammatory disorders, is provided.

17 Claims, No Drawings

OTHER PUBLICATIONS

Trosko et al. in Mutation Research, 480-481, pp. 219-229, 2001.
Gonzalez-Rothi et al., Pharmaceutical Research, vol. 13. No. 11 1996, pp. 1699-1703.
Office Action for U.S. Appl. No. 10/455,257, dated Aug. 9. 2004.
Office Action for U.S. Appl. No. 10/455,257, dated Mar. 3, 2005.
Office Action for U.S. Appl. No. 10/455,257, dated Oct. 3, 2005.
Office Action for U.S. Appl. No. 10/455,257, dated May 4, 2006.
Office Action for U.S. Appl. No. 10/455,257, dated Jul. 13, 2007.
Office Action for U.S. Appl. No. 10/455,257, dated Dec. 3, 2007.
Office Action for U.S. Appl. No. 10/455,257, dated Oct. 8, 2008.
Office Action for U.S. Appl. No. 10/455,257, dated Jun. 5, 2009.
Office Action for U.S. Appl. No. 10/455,257, dated Jan. 5, 2010.
Banciu et al., Liposomal glucocorticoids as tumor-targeted anti-angiogenic nanomedicine in B16 melanoma-bearing mice. Journal of Steroid Biochemistry and Molecular Biology, 2008, pp. 101-110, vol. 111.
Herr et al., Glucocorticoid use in prostate cancer and other solid tumours: implications for effectiveness of cytotoxic treatment and metastases. Lancet Oncol., 2006, pp. 425-430, vol. 7.
Rutz et al., Effects of corticosteroid use on treatment of solid tumours, The Lancet, Dec. 14, 2002, pp. 1969-1970, vol. 360.
U.S. Appl. No. 11/065,692, filed Feb. 24, 2005, Schiffelers et al., Vesicle-Encapsulated Corticosteroids for the Treatment of Cancer.

\* cited by examiner

COMPOSITION FOR TREATMENT OF INFLAMMATORY DISORDERS

CROSS-REFERENCE TO RELATED APPLICATION

This application is a continuation of PCT International Patent Application No. PCT/EP01/14633 filed on Dec. 7, 2001, designating the United States of America, and published, in English, as PCT International Publication No. WO 02/45688 A2 on Jun. 13, 2002, the contents of the entirety of which is incorporated by this reference.

TECHNICAL FIELD

The invention relates generally to pharmaceutical compositions, and more particularly to a pharmaceutical composition for parenteral and intravenous administration, comprising liposomes composed of non-charged vesicle-forming lipids, including up to about 20 mole percent of an amphipathic vesicle-forming lipid derivatized with polyethyleneglycol (PEG) and optionally including not more than 10 mole percent of negatively charged vesicle-forming lipids, the liposomes having a selected mean particle diameter in the size range between about 40-200 nm and containing a corticosteroid for the site-specific treatment of inflammatory disorders.

BACKGROUND OF THE INVENTION

Intravenous administration of compositions based on PEG-containing liposomes for the site-specific treatment of inflamed tissues and regions is already disclosed in EP-0662820. It is well known that long-circulating small-sized liposomes which contain non-charged or slightly negatively charged vesicle-forming lipids, such as PEG-liposomes, after intravenous administration can circulate for many hours in a volume not larger than the general circulation and therefore, in theory, are able to deliver relatively high portions of anti-inflammatory agents via extravasation at sites of enhanced vascular permeability common to inflamed regions. Such liposomes are of particular interest in the treatment of inflammatory diseases, e.g., rheumatoid arthritis, which is a chronic autoimmune disorder, causing joint inflammation and progressive cartilage destruction. Although several types of anti-rheumatic drugs are available for use, the treatment of severe, persistent synovitis and acute exacerbations may require the use of several intravenous injections containing high doses of glucocorticoids. Although systemic corticosteroids can suppress the symptoms of the disease, adverse effects limit their use. In addition to this, glucocorticoids suffer from unfavorable pharmacokinetic behavior: short plasma half-life values and a large distribution volume require high and repeated administration in order to reach a therapeutically effective concentration of the drug at the desired site of action. Intra-articular injection of steroids into the affected joints is often used to increase the local efficacy of the glucocorticoids and diminish the systemic adverse effects, but this way of administration is less comfortable for the patients and not feasible when multiple small joints are affected.

Also, a significant incidence of painless destruction of the joint may be associated with repeated intra-articular injections of glucocorticoids. According to EP-0662820-B, preferred compounds for entrapment in PEG-containing liposomes are the steroidal anti-inflammatory compounds, such as prednisone, methylprednisolone, paramethazone, 11-fludrocortisol, triamcinolone, betamethasone and dexamethasone. The steroids listed belong to the group of steroids which are systemically administered. Example No. 12 is the only example of a glucocorticoid-containing PEG-liposome in this patent and relates to the preparation of beclomethasone dipropionate-containing PEG-liposomes. However, no in vivo data were provided. On preparing dexamethasone-containing PEG-liposomes according to the disclosure in EP-0662820 and on intravenous administration of the same in an in vivo experimental arthritis model, the present inventors noted that the beneficial effects, as taught in EP-0662820, could not be observed at all. There was no difference in pharmacokinetic profile between a suspension containing the glucocorticoid and the PEG-liposomes in which the same glucocorticoid had been encapsulated.

Since glucocorticoids often are the most effective drugs in the treatment of inflammatory disorders, there is a need to provide liposomal compositions which after parenteral administration can more efficiently deliver effective amounts of glucocorticoid at the inflamed region or tissue for enhanced and prolonged local activity.

BRIEF SUMMARY OF THE INVENTION

The invention provides a pharmaceutical composition for parenteral administration, comprising liposomes composed of non-charged vesicle-forming lipids, including up to 20 mole percent of an amphipathic vesicle-forming lipid derivatized with polyethyleneglycol and optionally including not more than 10 mole percent of negatively charged vesicle-forming lipids, the liposomes having a selected mean particle diameter in the size range between about 40-200 nm and containing a water soluble corticosteroid for the site-specific treatment of inflammatory disorders.

The invention also provides a use of a pharmaceutical composition, comprising liposomes composed of non-charged vesicle-forming lipids, including up to 20 mole percent of an amphipathic vesicle-forming lipid derivatized with polyethyleneglycol and optionally including not more than 10 mole percent of negatively charged vesicle-forming lipids, the liposomes having a selected mean particle diameter in the size range between about 40-200 nm and containing a corticosteroid, for the preparation of a medicament effective in the site-specific treatment of inflamed tissues or regions after parenteral administration, characterized in that the corticosteroid is used in the medicament in a water soluble form.

DETAILED DESCRIPTION OF THE INVENTION

It has now been found that by incorporating a water soluble form of a corticosteroid in long-circulating liposomes, composed of non-charged vesicle-forming lipids, including up to 20 mole percent of amphipathic vesicle-forming lipids derivatized with polyethylene glycol (PEG) and optionally including not more than 10 mole percent of negatively charged vesicle-forming lipids, the liposomes having a selected mean particle diameter in the size range between about 40-200 nm, an increased localization and improved retention of the corticosteroid at inflamed tissue after one single intravenous injection of a pharmaceutical composition comprising the liposomes, can be reached as compared with one single intravenous injection of an aqueous solution containing the same corticosteroid compound.

The long-circulation liposomes according to the present invention have a circulation half life of at least 6 hours, the circulation half life being defined as the time at which the second linear phase of the logarithmic liposomal clearance profile reaches 50% of its initial concentration, which is the extrapolated plasma concentration at t=0.

The particle size of the liposomes is an important feature, which was demonstrated by the fact that administration of a water soluble corticosteroid, such as prednisolone disodium phosphate, in PEG-liposomes, having a mean particle diameter >500 nm, did not result in a significant decrease of paw inflammation in the rat adjuvant arthritis model.

A water soluble corticosteroid in accordance with the present invention is a compound which is soluble 1 in ≦10 (w/v), as assessed in water or water buffered at physiologic values, e.g. at pH>6.0, at a temperature between 15° and 25° C.

Water soluble corticosteroids which can be advantageously used in accordance with the present invention are alkali metal and ammonium salts prepared from corticosteroids, having a free hydroxyl group, and organic acids, such as ($C_2$-$C_{12}$) aliphatic saturated and unsaturated dicarbonic acids, and inorganic acids, such as phosphoric acid and sulfuric acid. Also, acid addition salts of corticosteroids can advantageously be encapsulated in the long-circulating PEG-liposomes. If more than one group in the corticosteroid molecule is available for salt formation, mono- as well as di-salts may be useful. As alkaline metal salts, the potassium and sodium salts are preferred. Also, other positively or negatively charged derivatives of corticosteroids can be used. Specific examples of water soluble corticosteroids are betamethasone sodium phosphate, desonide sodium phosphate, dexamethasone sodium phosphate, hydrocortisone sodium phosphate, hydrocortisone sodium succinate, methylprednisolone disodium phosphate, methylprednisolone sodium succinate, prednisolone sodium phosphate, prednisolone sodium succinate, prednisolanate hydrochloride, prednisone phosphate, triamcinolone acetonide disodium phosphate and triamcinolone acetonide dipotassium phosphate.

The above-mentioned corticosteroids normally are used in systemic treatment of anti-inflammatory diseases and disorders. Since it has been proven by the present inventors that by using a water soluble form of a corticosteroid in PEG liposomes, having a specified small mean particle diameter, effective targeting of the drug to arthritic sites, by systemic administration, occurs, the present invention can advantageously be applied to corticosteroids, which, for a variety of reasons, normally are used for topical use. Such corticosteroids include, for example, alclomethasone dipropionate, amcinonide, beclomethasone monopropionate, betamethasone 17-valerate, ciclomethasone, clobetasol propionate, clobetasone butyrate, deprodone propionate, desonide, desoxymethasone, dexamethasone acetate, diflucortolone valerate, diflurasone diacetate, diflucortolone, difluprednate, flumetasone pivalate, flunisolide, fluocinolone acetonide acetate, fluocinonide, fluocortolone pivalate, fluormetholone acetate, fluprednidene acetate, halcinonide, halometasone, hydrocortisone acetate, medrysone, methylprednisolone acetate, mometasone furoate, parametasone acetate, prednicarbate, prednisolone acetate, prednylidene, rimexolone, tixocortol pivalate and triamcinolone hexacetonide. Topical corticosteroids, which undergo fast, efficient clearance as soon as these drugs become available in the general circulation, are of special interest. Examples thereof are budesonide, flunisolide and fluticasone propionate. By preparing a water soluble form of the above-mentioned topical steroids and encapsulating this into PEG liposomes in accordance with the present invention, it is now possible to systemically administer such corticosteroids in order to reach site-specific drug delivery, thereby avoiding adverse effects associated with systemic treatment and overcoming problems, which are inherent to the corticosteroid, such as a fast clearance. In this respect, budesonide phosphate has appeared to be a salt of great interest.

The liposomes in accordance with the present invention may be prepared according to methods used in the preparation of conventional liposomes and the PEG-liposomes, as disclosed in e.g. EP-0662820. Passive loading of the active ingredients into the liposomes by dissolving the corticosteroid in the aqueous phase is sufficient in order to reach an encapsulation as high as possible, but other methods can also be used. The lipid components used in forming the liposomes may be selected from a variety of vesicle-forming lipids, such as phospholipids, sphingolipids and sterols. Substitution (complete or partial) of these basic components by e.g. sphingomyelines and ergosterol appeared to be possible. For effective encapsulation of the water soluble corticosteroids in the liposomes, thereby avoiding leakage of the drug from the liposomes, especially phospholipid components having saturated, rigidifying acyl chains, have appeared to be useful.

The beneficial effects observed after one single injection of the water soluble corticosteroid containing PEG liposomes according to the invention are very favorable when compared with the results obtained after single, but also repeated injections of the non-encapsulated water soluble corticosteroid in different concentrations. Administration of the non-encapsulated water soluble corticosteroid was much less effective than the encapsulated corticosteroid, which can be easily understood if the total amount of free versus encapsulated corticosteroid is considered: the free corticosteroid was always by a factor of at least 5-10 less effective, even when injected on 7 consecutive days. These effects have been observed in two different animal models, viz. a rat adjuvant arthritis model and a mouse model of collagen induced arthritis. The favorable effects may be a complete and long-lasting remission of all arthritis-associated symptoms, dependent of the dose. In addition thereto, in the mouse model, a reduced cartilage erosion was observed one week after treatment at the time the inflammation had returned again.

Since in Experimental Autoimmune Encephalomyelitis ultra high doses of methylprednisolone have been shown to be more efficient in induction of T cell apoptosis than the "standard" dose of 10 mg/kg used in multiple sclerosis therapy, it has been investigated whether a long-circulating liposome formulation containing prednisolone is superior to methylprednisolone pulse therapy in induction of T cell apoptosis in situ. It has been observed that liposomal prednisolone phosphate given at 10 mg/kg augments T cell apoptosis in situ rapidly and the reduced infiltration of T cells and macrophages leads to an ameliorated disease activity of Adoptive Transfer Experimental Autoimmune Encephalomyelitis (AT-EAE). As the liposomes can extravasate and accumulate in inflamed tissue with a disrupted blood-brain-barrier, liposomal prednisolone phosphate could be a therapeutic alternative to methylprednisolone, which needs a higher dosage and would therefore cause more systemic side-effects. These findings may have implications for the treatment of inflammatory autoimmune diseases of the Central Nervous System (CNS) such as multiple sclerosis.

Surprisingly, although small, rigid PEG-containing liposomes are known to hardly release their contents, the PEG-liposomes according to the present invention were able to effectively deliver the water soluble corticosteroid at the desired site of action resulting in a complete remission of the inflammation.

The following examples further illustrate the invention.

EXAMPLES

Example I

Preparation of Prednisolone Phosphate-Containing PEG-Liposomes 750 mg of dipalmitoyl phosphatidylcholine (DPPC) (Lipoid Ludwigshafen), 250.8 mg of cholesterol (Sigma Aldrich) and 267.6 mg of PEG-distearoylphosphatidylethanolamine (PEG-DSPE) (Avanti Polar Lipids) were weighed and mixed in a 100 ml round-bottom flask. The lipids were dissolved in about 30 ml of ethanol. Thereafter, evaporating to dryness in a Rotavapor during 1 hour under vacuum at 40° C., followed by flushing with nitrogen gas during 1 hour took place.

1200 mg of prednisolone disodium phosphate (OPG Nieuwegein) were weighed and dissolved in 12 ml of sterilized PBS. The solution was added to the dry lipid film and shaken for one hour in the presence of glass beads in order to enable complete hydration of the lipid film.

The liposomal suspension was transferred to an extruder (Avestin, maximum volume 15 ml) and extruded under pressure, using nitrogen gas, 6 times through 2 pore filters one placed on top of the other, having a pore size of 200 and 100 nm respectively, 100 and 50 nm respectively, and 50 and 50 nm respectively. Subsequently the liposomal suspension was dialyzed in a dialyzing compartment (Slide-A-Lyzer, 10.000 MWCO) 2 times during 24 hours against 1 liter of sterilized PBS.

The mean particle size of the liposomes was determined by means of light scattering (Malvern Zeta-sizer) and was found to be $93.1\pm1.2$ nm, the polydispersity index being $0.095\pm0.024$. The encapsulation efficiency of the prednisolone phosphate was determined by means of a HPLC method and was found to be between 3 and 4%. The suspension of liposomes was stored in a nitrogen atmosphere at 4° C. and found to be stable for about 2 months.

Example II

Preparation of Other Water Soluble Corticosteroid Containing PEG-Liposomes

Example I was repeated but instead of prednisolone disodium phosphate dexamethasone disodium phosphate (OPG Nieuwegein), betamethasone disodium phosphate (Sigma-Aldrich) or budesonide 21-phosphate (prepared by Syncom, Groningen, the Netherlands) respectively was used.

Example III

Assessment of Therapeutic Efficacy in Rat Adjuvant Arthritis Model

Lewis rats were immunized subcutaneously at the tail base with heat-inactivated *Mycobacterium tuberculosis* in incomplete Freund's adjuvant. Paw inflammation started between 9 and 12 days after immunization, reached maximum severity approximately after 20 days, and then gradually resolved.

Assessment of the disease was performed by visually scoring paw inflammation severity, maximum score 4 per paw, and measuring disease-induced body weight loss. The therapeutic efficacy of liposomal prednisolone phosphate, prepared according to example 1, on these variables was compared with equal doses unencapsulated drug. Rats were treated when the average score >6 (at day 14 or 15 after disease induction).

A complete remission of the inflammation process in 4 out of 5 rats was observed within 3 days after treatment with a single dose 10 mg/kg liposomal prednisolone phosphate (average score $0.1\pm0.1$, compared to $11.8\pm1.9$ of the PBS-treated rats). Unencapsulated prednisolone phosphate did not significantly alter the course of the disease ($p>0.05$, Kruskall-Wallis test, non-parametric). In contrast, also 1 mg/kg liposomal prednisolone phosphate was effective ($p<0.05$, Kruskall-Wallis, non-parametric). With respect to weight loss, only 10 mg/kg liposomal prednisolone phosphate had a significant effect ($p<0.05$, one-way ANOVA). Within 8 days, these rats regained initial weight. Other treatment groups continued suffering from progressive weight loss.

No effect of a single injection unencapsulated prednisolone phosphate was observed. Therefore, it was decided to inject 10 mg/kg and 20 mg/kg daily for 7 days. Both treatment regimens reduced inflammation scores from an average of $6.5\pm0.56$ (day 14) to average values around 5.0 from day 15 until day 21 (control treatment with daily saline reached a maximum of $10.6\pm1.3$ on day 20). However, single injections of 10 mg/kg and 20 mg/kg liposomal prednisolone phosphate at day 14 resulted in disappearance of adjuvant arthritis (AA) symptoms until day 20. Control treatment with empty liposomes did not result in an altered progression of the disease ($p>0.05$).

The liposomal compositions of example 2 were also tested in the adjuvant arthritis model. Liposomal dexamethasone phosphate proved to be more effective than either liposomal prednisolone phosphate or liposomal betamethasone phosphate. A dose of 2 mg/kg was equally effective as 10 mg/kg liposomal prednisolone phosphate. 2 mg/kg liposomal betamethasone phosphate proved to be more effective than 2 mg/kg liposomal prednisolone phosphate, however, in contrast to 2 mg/kg liposomal dexamethasone phosphate, no complete reversal was obtained. Liposomal budesonide 21-phosphate (1 mg/kg) produced at least equally effective disease suppression as compared to liposomal dexamethasone phosphate.

Example IV

Assessment of Therapeutic Efficacy in AT-EAE

Adoptive Transfer Experimental Autoimmune Encephalomyelitis (AT-EAE) was induced in female Lewis rats by intravenous injection of $10^7$ MBP-specific T cells.

10 mg/kg prednisolone phosphate containing liposomes, as prepared according to Example I, were applied intravenously at 42 hours and 18 hours prior to sacrifice. Another group received 50 mg/kg methylprednisolone intravenously at 18 hours and 6 hours before perfusion. Control rats received empty liposomes and/or saline at equivalent time points.

T cells or macrophages in spinal cord were detected immunohistochemically in paraffin embedded tissue and apoptosis was assessed by the TUNEL assay and by morphological criteria. Student t test for grouped data was used for statistical analysis. The rate of T cell apoptosis in spinal cord tissue was significantly augmented by liposomal prednisolone phosphate ($39.4\pm6.8\%$, $p<0.0001$ vs. $16.1\pm4.3\%$ in the control group, all data given as mean±SD). Methylprednisolone as an internal control lead to a rate of $30.8\pm8.0\%$ T cell apoptosis ($p<0.01$ vs. Controls). As a result of the increase in apoptosis, T cell infiltration was clearly reduced by liposomal prednisolone phosphate (45±12 T cells/mm$^2$), which was statistically significant compared to controls (115±51 T cells/mm$^2$, $p<0.05$) as well as compared to methylprednisolone (96±19 T cells/mm$^2$, $p<0.05$). As another aspect of inflammation the macrophage infiltration was significantly reduced by liposomal prednisolone phosphate (31±13 macrophages/mm$^2$) compared to controls (78±37 macrophages/mm$^2$, $p<0.05$) and compared to methylprednisolone (66±25 macrophages/mm$^2$, $p<0.05$). Even though the Adoptive Transfer model was chosen to investigate rapid mechanisms, a therapeutic benefit from liposomal prednisolone phosphate could be observed within 42 hours, achieving a clinical score of 2.8±0.2 compared to controls (3.2±0.3, $p<0.01$), which was superior to methylprednisolone (3.2±0.3, $p<0.05$ vs. liposomal prednisolone phosphate).

What is claimed is:

1. A pharmaceutical composition comprising:
   a corticosteroid in water-soluble form having a water solubility of at least 1 in <10 (w/v), as assessed in water or water buffered at physiologic values, and
   negatively charged liposomes consisting of cholesterol, non-charged vesicle-forming lipids, amphipathic vesicle-forming lipids derivatized with polyethyleneglycol, said amphipathic vesicle-forming lipids being present in an amount of up to 10 mole percent, and up to 10 mole percent of negatively charged vesicle-forming lipids,
   wherein said negatively charged liposomes have a selected mean particle diameter in a size range between about 40-200 nm and enclose said corticosteroid.

2. The pharmaceutical composition of claim 1, wherein the corticosteroid comprises a systemically administered corticosteroid.

3. The pharmaceutical composition of claim 2, wherein the systemically administered corticosteroid in water-soluble form is selected from the group consisting of water-soluble forms of prednisolone, dexamethasone, methylprednisolone, and mixtures thereof.

4. The pharmaceutical composition of claim 1, wherein the corticosteroid in water-soluble form is selected from the group consisting of water-soluble forms of budesonide, flunisolide, fluticasone, and mixtures thereof.

5. A method for parenteral treatment of inflamed tissues or regions in a subject, the method comprising:
   administering to the subject a pharmaceutical composition comprising:
   a corticosteroid in water-soluble form having a water solubility of at least 1 in <10 (w/v), as assessed in water or water buffered at physiologic values, and
   negatively charged liposomes consisting of cholesterol, non-charged vesicle-forming lipids, amphipathic vesicle-forming lipids derivatized with polyethyleneglycol, said amphipathic vesicle-forming lipids being present in an amount of up to 10 mole percent, and up to 10 mole percent of negatively charged vesicle-forming lipids,
   wherein the liposomes have a selected mean particle diameter in a size range between about 40-200 nm and enclose said corticosteroid and wherein said liposomes are negatively charged,
   thus targeting said liposomes selectively to sites of enhanced vascular permeability common to inflamed regions.

6. The method according to claim 5, wherein the corticosteroid comprises a systemically effective corticosteroid.

7. The method according to claim 5, wherein the corticosteroid comprises a corticosteroid selected from the group consisting of water-soluble forms of budesonide, flunisolide, fluticasone propionate, and mixtures thereof.

8. The method according to claim 5 for the site-specific treatment of rheumatoid arthritis in the subject.

9. The method according to claim 6 for the site-specific treatment of rheumatoid arthritis in the subject.

10. The method according to claim 7 for the site-specific treatment of rheumatoid arthritis in the subject.

11. The method according to claim 5 for the site-specific treatment of multiple sclerosis in the subject.

12. The method according to claim 6 for the site-specific treatment of multiple sclerosis in the subject.

13. The method according to claim 7 for the site-specific treatment of multiple sclerosis in the subject.

14. A parenteral pharmaceutical composition for alleviating symptoms associated with rheumatoid arthritis or multiple sclerosis in a subject, said parenteral pharmaceutical composition comprising:
   a corticosteroid in water-soluble form, said corticosteroid selected from the group consisting of budesonide, flunisolide, fluticasone, prednisolone, dexamethasone, methylprednisolone, and mixtures thereof,
   negatively charged liposomes consisting of cholesterol, non-charged vesicle-forming lipids, amphipathic vesicle-forming lipids derivatized with polyethyleneglycol, said amphipathic vesicle-forming lipids being present in an amount of up to 10 mole percent, and
   up to 10 mole percent of negatively charged vesicle-forming lipids,
   wherein said negatively charged liposomes have a selected mean particle diameter in a size range of between about 40 and about 200 nm and enclose said corticosteroid.

15. An improvement in a pharmaceutical composition of the type comprising a corticosteroid enclosed within liposome, wherein the improvement comprises:
   utilizing, as the corticosteroid, a corticosteroid in a water-soluble form having a water solubility of at least 1 in <10 (w/v), as assessed in water or water buffered at physiologic values,
   wherein the liposome is negatively charged and consists of cholesterol, non-charged vesicle-forming lipids, amphipathic vesicle-forming lipids derivatized with polyethyleneglycol, said amphipathic vesicle-forming lipids being present in an amount of up to 20 mole percent, and up to 10 mole percent of negatively charged vesicle-forming lipids, and
   wherein the liposomes enclose said corticosteroid and are negatively charged.

16. A pharmaceutical composition comprising:
   a corticosteroid in water-soluble form having a water solubility of at least 1 in <10 (w/v), as assessed in water or water buffered at physiological values, and
   negatively charged liposomes consisting of cholesterol, non-charged vesicle-forming lipids, amphipathic vesicle-forming lipids derivatized with polyethyleneglycol, said amphipathic vesicle-forming lipids comprising distearoylphosphatidylethanolamine and being present in an amount of up to 10 mole percent, and up to 10 mole percent of negatively charged vesicle-forming lipids,
   wherein said negatively charged liposomes have a selected mean particle diameter in a size range between about 40-200 nm and enclose said corticosteroid.

17. A pharmaceutical composition comprising:
   a corticosteroid in water-soluble form having a water solubility of at least 1 in <10 (w/v), as assessed in water or water buffered at physiologic values, and negatively charged liposomes consisting of cholesterol, non-charged vesicle-forming lipids, amphipathic vesicle-forming lipids derivatized with polyethyleneglycol, said amphipathic vesicle-forming lipids comprising dipalmitoyl phosphatidylcholine and being present in an amount of up to 10 mole percent, and up to 10 mole percent of negatively charged vesicle-forming lipids, wherein said negatively charged liposomes have a selected mean particle diameter in a size range between about 40-200 nm and enclose said corticosteroid.

* * * * *